United States Patent [19]

Wolf

[11] Patent Number: 4,586,31[5]

[45] Date of Patent: May 6, 198[6]

[54] APPARATUS FOR INTRODUCING STACKS OF PAPER LAYERS INTO CARTONS

[75] Inventor: Wolfram Wolf, Bilsen, Fed. Rep. of Germany

[73] Assignee: E.C.H. Will (GmbH & Co.), Hamburg, Fed. Rep. of Germany

[21] Appl. No.: 630,928

[22] Filed: Jul. 16, 1984

[30] Foreign Application Priority Data

Jul. 14, 1983 [DE] Fed. Rep. of Germany ....... 3325378

[51] Int. Cl.$^4$ ........................ B65B 35/50; B65B 39/12
[52] U.S. Cl. ...................................... 53/447; 53/245; 53/536
[58] Field of Search ................. 53/244, 245, 447, 495, 53/531, 535, 536, 540; 271/189, 192, 217, 218; 414/48, 49, 82, 85, 98, 100

[56] References Cited

U.S. PATENT DOCUMENTS

| | | | |
|---|---|---|---|
| 2,956,384 | 10/1960 | Underwood | 53/244 |
| 4,138,836 | 2/1979 | Crowe et al. | 53/535 |
| 4,237,674 | 12/1980 | Aykut | 53/249 |
| 4,249,844 | 2/1981 | Lampe et al. | 414/45 |

FOREIGN PATENT DOCUMENTS

| | | | |
|---|---|---|---|
| 2705509 | 8/1978 | Fed. Rep. of Germany | 414/49 |
| 0115878 | 9/1979 | Japan | 414/82 |

Primary Examiner—James F. Coan
Attorney, Agent, or Firm—Peter K. Kontler

[57] ABSTRACT

Apparatus for accumulating stacks of superimposed layers or piles of paper sheets has a horizontal platform which receives successive layers from a feeding unit and can open up to permit the properly oriented layer thereon to descend by gravity onto an elevator which is disposed at a level below the platform and at a distance only slightly exceeding the height of a layer. The elevator is then lowered by a step, and the platform receives and discharges the next layer in the same way so that the elevator supports two layers. The accumulation of layers on the elevator is repeated as often as desired in order to accumulate a stack of desired height. The elevator is then opened and permits the fully grown stack to descend through a chute and into a container (such as a carton which is disposed therebelow and is properly centered by a suitable receptacle). The descent of the stack is braked by the column of air which is pushed by the stack in front of it through the chute and into the interior of the carton. The platform comprises two panels which are movable laterally away from each other to permit a layer to descend from the platform onto the elevator or onto the topmost layer on the elevator.

13 Claims, 2 Drawing Figures

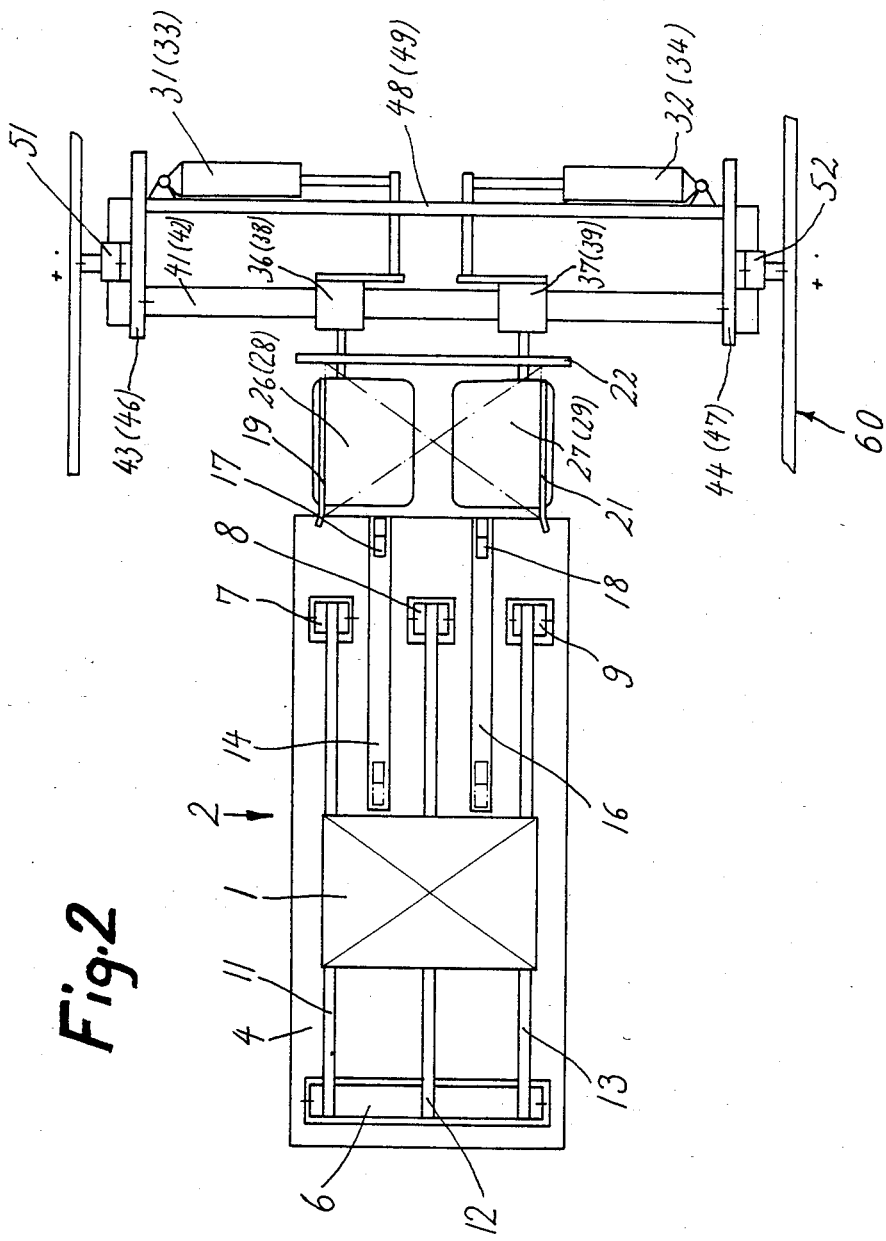

APPARATUS FOR INTRODUCING STACKS OF PAPER LAYERS INTO CARTONS

CROSS-REFERENCE TO RELATED CASES

The apparatus of the present invention is somewhat similar to apparatus which are disclosed in commonly owned U.S. Pat. Nos. 4,237,674 and 4,249,844 and in commonly owned copending U.S. patent application Ser. No. 473,732 filed Mar. 9, 1983 by Kurt Aykut et al, now U.S. Pat. No. 4,520,614 granted June 4, 1985.

BACKGROUND OF THE INVENTION

The present invention relates to improvements in apparatus for introducing stacks of sheets into cartons or other types of containers. More particularly, the invention relates to improvements in apparatus for accumulating discrete sheets or layers of superimposed sheets into stacks of superimposed discrete sheets or layers prior to admission of the thus accumulated stacks into cartons or other types of containers.

It is already known to accumulate layers of paper sheets or the like into stacks of superimposed layers prior to introduction of the thus obtained stacks into cartons or like containers. For example, German Utility Model No. 82 06 480.6 discloses an apparatus having a feeding conveyor which delivers a succession of layers into the open upper end of a duct wherein the layers descend and land on top of a bottom wall which is normally closed. When the bottom wall intercepts a predetermined number of layers, i.e., when it accumulates a fully grown stack of paper sheets or the like, the bottom wall is caused to open and to thus drop the fully grown stack whereby the latter descends by gravity through the open top of and into the interior of a container (such as a cardboard carton) therebelow. The bottom wall of the duct includes two sheet metal panels which are movable apart so as to provide a passage for gravitational descent of the fully grown stack.

A drawback of the just described conventional apparatus is that successive layers, and especially the lowermost layers, of a growing stack in the duct must descend by gravity through a considerable distance before they strike the top surface of the closed bottom wall in the deepmost region of the duct or the topmost layer on the closed bottom wall. This can lead to misalignment of layers in the interior of the duct and in the interior of the container. Therefore, the German Utility Model proposes to provide the duct with a vibrator which shakes the duct during introduction and dwell of layers on top of the closed bottom wall and to thus enhance the likelihood of the formation of a stack wherein the layers are accurately aligned with and fully overlap each other. As a rule, the dimensions of the duct closely approximate the desired dimensions of the stack which is to be accumulated therein.

It has been found that mere shaking of the duct and/or the bottom wall, even in conjunction with the aforediscussed dimensioning of the duct, does not suffice to invariably ensure the formation of accurately formed stacks and predictable introduction of stacks into cartons or analogous containers. Furthermore, the provision of one or more vibrators entails continuous consumption of electrical or other energy and the vibrator or vibrators generate noise which is unpleasant to the workers and can affect their health and/or ability to concentrate.

OBJECTS AND SUMMARY OF THE INVENTION

An object of the invention is to provide a novel and improved apparatus which can properly accumulate tall or short stacks of superimposed paper sheets or the like with the same degree of accuracy and predictability.

Another object of the invention is to provide an apparatus whose operation is practically noiseless or which generates much less noise than the aforediscussed conventional apparatus.

A further object of the invention is to provide an apparatus which need not be equipped with one or more vibrators for the purpose of accurately stacking layers of paper sheets or the like.

Still another object of the invention is to provide the apparatus with novel and improved means for reducing the likelihood of misalignment of successively delivered layers of paper sheets or the like during the accumulation of a stack.

A further object of the invention is to provide the apparatus with novel and improved means for properly orienting individual layers as well as for properly orienting partially or fully grown stacks prior to and during their introduction into cartons or other types of containers.

A further object of the invention is to provide the apparatus with novel and improved means for ensuring the accumulation of stacks in a small area, with little loss in time and with a heretofore unmatched degree of accuracy and reproducibility.

An additional object of the invention is to provide an apparatus which can be utilized in existing production lines for the accumulation of stacks as well as for packing of stacks of paper sheets or the like as a superior substitute for heretofore known stack forming and processing apparatus.

Another object of the invention is to provide 9 novel and improved method of manipulating layers of paper sheets or the like on their way from the sheet cutting to the packing station.

An additional object of the invention is to provide a method which can be practiced with resort to relatively simple, compact, inexpensive and rugged apparatus.

One feature of the invention resides in the provision of an apparatus for accumulating stacks of sheet-like commodities in containers of the type having an open side. The apparatus comprises a platform, means for moving the platform between an operative position in which the platform can support a commodity and an inoperative position in which the platform allows a commodity thereon to descend by gravity, an elevator which is disposed below the platform, means for moving the elevator up and down nearer to and further away from the platform, means for positioning discrete containers below the elevator so that the open side of the container below the elevator faces upwardly, means for moving the elevator between an intercepting position in which the elevator can receive a succession of commodities in response to repeated movements of the platform to its inoperative position and a releasing position in which the stack of commodities which has accumulated on the elevator in response to repeated movements of the platform to its inoperative position is free to descend into the container therebelow, and means for feeding commodities seriatim onto the platform while the platform assumes the operative position.

The feeding means defines for the commodities a predetermined path which is preferably at least substantially horizontal, and the platform is preferably located at the level of such path.

The improved apparatus preferably further comprises an at least substantially upright duct which is disposed below the platform but above the container in or on the positioning means. The elevator is movable up and down in the interior of such duct, i.e., the sides of the growing stack in the duct are confined while the height of the stack increases until it reaches the ultimate or final height, for example, a height matching the combined thickness of five reams of paper sheets.

The elevator is preferably movable to and from a predetermined lower end position rather close to the open top of the container therebelow. Such apparatus preferably further comprises means for guiding the stacks of commodities from the elevator into the container in or on the positioning means on movement of the elevator to its releasing position and while the elevator assumes or is close to the lower end position. Such guiding means can comprise an at least substantially upright chute or duct. In order to ensure proper orientation of successive commodities which are delivered by the feeding means onto the upper side of the platform while the latter assumes its operative position, the apparatus preferably further comprises a set of walls which define a barrier that partially surrounds the platform and serves to locate successive oncoming commodities in predetermined positions with reference to the platform.

The means for moving the elevator up and down preferably comprises means for lowering the elevator in stepwise fashion through distances which need not appreciably exceed the height of a commodity, e.g., the height of a ream of superimposed paper sheets. It is preferred to construct the means for lowering the elevator in stepwise fashion in such a way that the lowering means can perform at least two but preferably more than three steps. This renders it possible to accumulate tall stacks.

Another feature of the invention resides in the provision of a method of accumulating stacks of sheet-like commodities in containers of the type having open tops. The method comprises the steps of advancing a series of discrete commodities along a predetermined (preferably horizontal or nearly horizontal) path, arresting successive foremost commodities in a predetermined position, preferably at the general level of the path, effecting a stepwise gravitational descent of a preselected number (e.g., five) of successive arrested commodities below the aforementioned level so that the first commodity of the preselected number descends alone and each following commodity descends with the preceding commodity or commodities so that the thus descending commodities accumulate into a stack of superimposed commodities, placing a container below the stack so that its open top faces upwardly, and effecting a gravitational descent of the fully grown stack into the container which is located below it. Such method preferably further comprises the step of imparting to each commodity a predetermined orientation in the course of the respective arresting step. Furthermore, the method can comprise the step of laterally confining the commodities in the course of the stack-accumulating step and/or of laterally confining the stack during descent of the stack into the container.

The novel features which are considered as characteristic of the invention are set forth in particular in the appended claims. The improved apparatus itself, however, both as to its construction and its mode of operation, together with additional features and advantages thereof, will be best understood upon perusal of the following detailed description of certain specific embodiments with reference to the accompanying drawing.

BRIEF DESCRIPTION OF THE DRAWING

FIG. 2 is a somewhat schematic plan view of the apparatus which is shown in FIG. 1.

DESCRIPTION OF THE PREFERRED EMBODIMENTS

Figure 1:
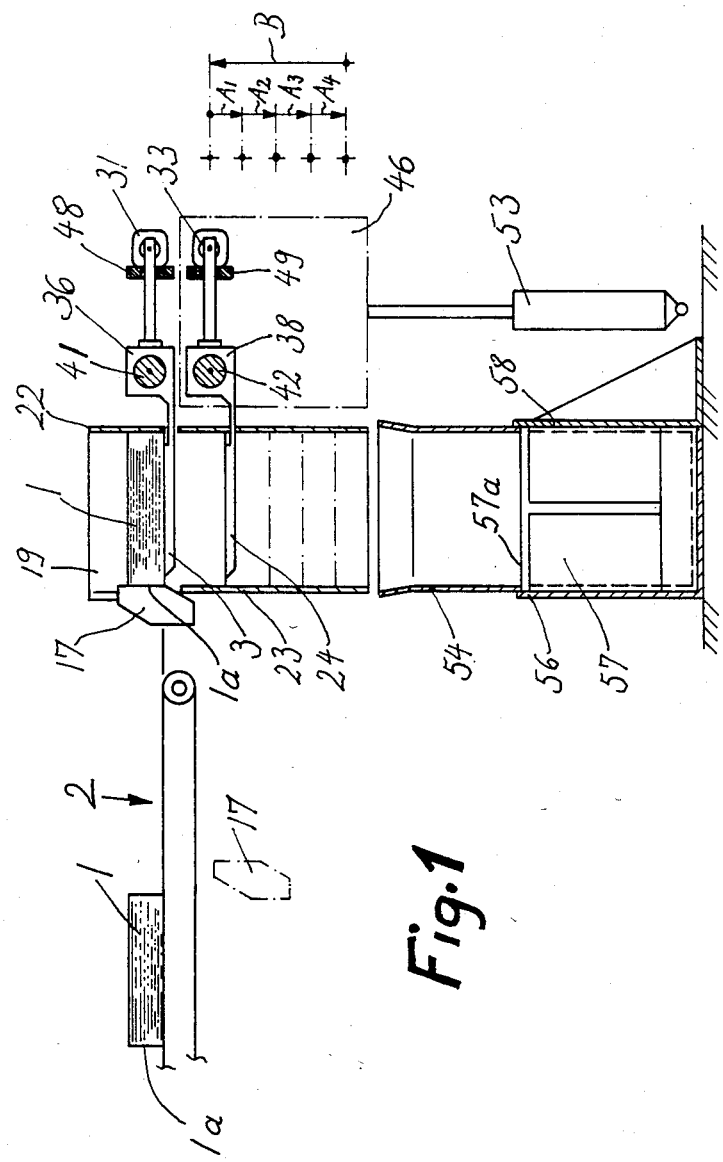
FIG. 1 is a somewhat schematic partly elevational and partly vertical sectional view of an apparatus which embodies one form of the invention and is designed to accumulate stacks each of which consists of five superimposed reams of paper sheets.

Referring to the drawing in detail, the improved apparatus comprises a feeding unit 2 which serves to advance a succession of discrete and preferably uniformly spaced-apart layers 1 of superimposed paper sheets in a direction to the right and onto the upper side of a stationary receiving platform 3. In the illustrated embodiment, the feeding unit 2 comprises a horizontal table 4 the upper side of which is flush with the upper side of the platform 3 and which has suitable cutouts for portions of endless belt conveyors 11, 12, 13. All of the three belt conveyors are trained over a common rear pulley 6, and these belt conveyors are trained over discrete front pulleys 7, 8, 9 respectively. The upper reaches of the belt conveyors 11, 12, 13 are disposed at the level of the upper side of the table 4 or at a level only slightly thereabove. The table 4 is further formed with two longitudinally extending elongated slots 14 and 16 which are respectively disposed between the planes of the belt conveyors 11, 12 and 12, 13 and serve to permit the passage of circulating advancing fingers or pushers 17, 18 respectively. The arrangement is such that each pusher rises to a level above the upper side of the table 4 when it is located at the rear end of the respective slot 14 or 16, and that each pusher descends to a level below the table 4 when it has reached the foremost end of its stroke. FIG. 1 shows by solid lines one of the pushers 17 in its raised position in which the pusher has completed its forward stroke and abuts against the rear edge face 1a of a layer 1 which has been properly transferred onto the upper side of the platform 3. The pusher 17 which is shown in FIG. 1 by phantom lines is about to rise to a level above the table 4 so as to engage the rear edge face 1a of the oncoming layer 1 and to push such layer, with assistance from the upper reaches of the belt conveyors 11, 12 and 13, toward and onto the platform 3. The means for moving the pushers 17, 18 and for driving the pulley 6 and/or the pulleys 7, 8 and 9 is not specifically shown in the drawing. In the illustrated embodiment, the upper side of the table 4 is at least substantially horizontal, the same as the upper side of the platform 3.

The improved apparatus further comprises a barrier which includes two upright sidewalls 19 and 21 at a level above the platform 3 and a rear wall 22 which faces the feeding unit 2 and arrests the oncoming layer 1. Such walls ensure proper orientation of each of a short or long series of layers 1 upon arrival of a layer onto the upper side of the platform 3.

The platform 3 is disposed at a level above an upright gathering duct 23 defining a space with a cross section matching that of a layer 1 so that a layer which descends from the platform 3 into the duct 23 is snugly received in the latter. The duct 23 receives a vertically movable elevator 24 which is similar to or identical with the platform 3. The only difference between the illustrated platform 3 and the illustrated elevator 24 is that the elevator is movable stepwise up and down in the interior of the duct 23 so as to gradually lower a growing stack of superimposed layers 1 toward the open lower end of the duct 23. As can be seen in FIG. 2, the platform 3 comprises two mirror symmetrical sections or panels 26 and 26 connected to discrete sleeves 36, 37 which are reciprocable along a horizontal guide member in the form of a tie rod 41. The end portions of the tie rod 41 are mounted in upright frame members 43 of the machine which embodies the improved apparatus. The elevator 24 comprises two sections or panels 28, 29 secured to sleeves 38, 39 which are reciprocable along a second horizontal guide member in the form of a tie rod 42 affixed to upright frame members 46, 47 of the aforementioned machine. The sleeves 36, 37 are respectively reciprocable by fluid-operated motors in the form of double-acting pneumatic cylinder and piston units 31 and 32. Similar fluid-operated motors 33, 34 are provided to respectively reciprocate the sleeves 38, 39 along the corresponding tie rod 42. When the motors 31, 32 are caused to retract their respective pistons into the corresponding cylinders, the sleeves 36, 37 move away from each other and thereby move the panels or sections 26, 27 apart so that a layer 1 which was supported by the upper sides of such panels is free to drop by gravity and to come to rest on the upper side of the elevator 24 or on the topmost sheet of a layer which is already supported by the elevator 24. When the elevator 24 is to receive the first of a series of five successive layers 1, its upper side is preferably closely adjacent to the underside of the platform 3; at such time, the distance between the upper side of the elevator 24 and the underside of the platform 3 need not appreciably exceed the height of a layer 1. This reduces the likelihood of misalignment of sheets which constitute a layer during gravitational descent from the panels 26, 27 onto the panels 28, 29.

The frame members 43, 44 are connected to each other by a reinforcing member or traverse 48. A similar reinforcing member or traverse 49 connects the frame members 46, 47 for the lower tie rod 42.

The frame members 46, 47 are respectively movable up and down along vertical guides 51, 52 which are mounted in the housing 60 of the paper processing machine. The means for moving the frame members 46, 47 and the corresponding tie rod 42 up and down in stepwise fashion (at least while moving downwardly) comprises a fluid operated motor 53 in the form of a pneumatic cylinder and piston unit (see the lower righthand portion of FIG. 1). The controls which cause the motor 53 to lower the elevator 24 in stepwise fashion and which cause the motors 31, 32, 33, 34 to perform their working and return strokes in synchronism with the operation of other parts of the illustrated apparatus and of the paper processing machine are not specifically shown in the drawing.

The apparatus further comprises a suitably configurated upright duct or chute 54 which is disposed below the lower end of the duct 23 and serves to laterally confine and guide a fully grown stack of layers 1 on its way into the interior of a carton 57 or another suitable container which is positioned in a receptacle 56 at the lower end of the chute 54. The rear wall 58 of the positioning means 56 is preferably removable or pivotable to an open position so as to allow for convenient insertion of an empty carton 57 or for withdrawal of a full carton from the positioning means. The open side 57a of the illustrated carton 57 constitutes an open top, and such open top faces the lower end of the duct 23.

The operation of the improved apparatus is as follows:

The feeding unit 2 delivers a succession of discrete layers 1 at selected intervals whereby the foremost layer enters the space above the stationary platform 3 between the side walls 19, 21 and rear wall 22. Such walls properly orient the layer 1 and bring it to a halt at a time when the layer is aligned with the open upper end of the duct 23 therebelow. At such time, the platform 3 is in operative position, i.e., its panels 26 and 27 are sufficiently close to each other (see FIG. 2) to properly support the lowermost sheet of a layer 1 thereon. This layer abuts against the rear wall 22 and is confined between the sidewalls 19 and 21 so that it is in full alignment with the duct 23. At such time, the motor 53 maintains the elevator 24 in the upper end position in which the elevator is close to but is still spaced apart from the underside of the platform 3. The distance between the platform 3 and the elevator 24 at least equals the height of a layer 1. The pushers 17 and 18 cooperate with the sidewalls 19, 21 and rear wall 22 to ensure proper orientation of a layer 1 which has been transferred onto the platform 3. Such pushers thereupon descend to a level below the table 4 and return to their rear end positions by moving counter to the direction of the oncoming layer 1 on the belts 11, 12, 13 of the feeding unit 2. When the pusher or pushers 17 and 18 are retracted from the layer 1 on the platform 3, the motors 31 and 32 are actuated in a sense to move the respective sleeves 36, 37 away from each other and to thus move the platform 3 to its inoperative position, i.e., the panels 26, 27 move apart and allow the freshly arrested and properly oriented layer 1 to descend by gravity onto the upper side of the elevator 24 which is held in its upper end position by the motor 53. The direction of movement of the piston rod of the motor 31, 32 is then reversed so that the sleeves 36, 37 move toward each other and return the platform 3 to its operative position in which the platform is ready to receive the next layer 1 from the feeding unit 2. The motor 53 is then actuated to lower the elevator 24 by a step 1A (shown in the righthand portion of FIG. 1) so as to provide room for the descent of a second layer 1 on top of the layer which is already supported by the elevator 24. The layer which has been received by the platform 3 in the meantime is thereupon dropped onto the layer which already rests on the elevator 24, the platform 3 is returned to its operative position, and the motor 53 lowers the elevator 24 by a step A2 so as to provide room for a third layer. The same operation is repeated again and again until the elevator 24 accumulates a stack of, for example, five superimposed layers. In other words, the illustrated apparatus is designed to enable the motor 53 to lower the elevator 24 four consecutive times (note the steps A1, A2, A3, A4). When the accumulation of a full stack is completed, the motors 33, 34 are actuated to move the respective sleeves 38, 39 away from each other and to thus move the elevator 24 to its retracted or discharging position by shifting the panels 28 and 29 away from each other. This enables the entire stack of five superimposed layers 1 to descend by gravity through the chute 54 and into the carton 57 in the positioning means 56. The motors 33, 34 thereupon return the panels 28, 29 to the positions in which such panels can properly support one or more layers 1 and the motor 53 is actuated to move the elevator 24 in the direction of arrow B shown in the right-hand portion of FIG. 1 and back to the upper end position. All this takes place before the platform 3 is again moved to its inoperative position so as to discharge the freshly received and properly oriented layer 1 onto the upper side of the elevator 24. The accumulation of the next stack then progresses in a manner as described above.

The gravity duct or chute 54 and the positioning means 56 act not unlike a damping cylinder, and the stack of five superimposed layers 1 which descend on opening of the elevator 24 acts not unlike a plunger or piston which pushes a column of air in front of it and into the interior of the container 57 in the positioning means 56. This ensures a highly desirable damping and ensuing gradual lowering or descent of the stack into the interior of the carton 57. When the stack is fully received in the carton 57, the rear wall 58 is removed or pivoted to open position and the freshly filled carton 57 is replaced with an empty carton whose open side or top 57a faces upwardly toward the lower end of the duct 23. The extent to which the air cushion which develops on gravitational descent of the stack from the duct 23 into the carton 57 brakes the descending stack can be selected practically at will by proper selection of the dimensions of the chute 54 and positioning means 56.

An important advantage of the improved apparatus is that the motor 53 can lower the elevator 24 in stepwise fashion. This ensures that a layer 1 which has been released by the platform 3 need not drop through a considerable distance but merely through a distance which equals or only slightly exceeds the height of a layer 1. This contributes to more accurate stacking of layers in the duct 23 preparatory to transfer of a fully grown layer into the carton 57 in the positioning means 56.

It has been found that the improved apparatus is capable of forming a long or short series of stacks with a very high degree of accuracy so that the stacks can be readily introduced into cartons that are only slightly larger than a stack. Furthermore, the apparatus is simple because the duct 23, the chute 54 and/or the positioning means 56 need not be vibrated in order to ensure accurate alignment of sheets which constitute the layers and the stacks. In fact, even without the provision of any vibrator or vibrators, the improved apparatus can be used to accumulate stacks at a frequency which exceeds the frequency of heretofore known apparatus.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of any contribution to the art and, therefore, such adaptations should and are intended to be comprehended within the meaning and range of equivalence of the appended claims.

I claim:

1. Apparatus for accumulating stacks of sheet-like commodities in containers of the type having an open side, comprising a platform; means for moving said platform between an operative position in which the platform can support a commodity and an inoperative position in which the platform allows a commodity thereon to descend by gravity; an elevator disposed below said platform; means for moving said elevator up and down nearer to and further away from said platform; means for positioning discrete containers below said elevator so that the open side of the container below said elevator faces upwardly; means for moving said elevator between an intercepting position in which the elevator can receive a succession of commodities in response to repeated movements of said platform to inoperative position and a releasing position in which the stack of commodities which have accumulated on said elevator in response to repeated movements of said platform to inoperative position is free to descend into the container therebelow; and means for feeding commodities seriatim onto the platform while the latter assumes said operative position.

2. The apparatus of claim 1, wherein said feeding means defines for the commodities a predetermined path and said platform is located at the level of said path.

3. The apparatus of claim 1, further comprising an at least substantially upright duct below said platform and above the container in said positioning means, said elevator being movable up and down in said duct.

4. The apparatus of claim 1, wherein said elevator is movable to and from a predetermined lower end position and further comprising means for guiding the stacks of commodities from said elevator into the container in said positioning means on movement of said elevator to said releasing position and in or close to the lower end position of said elevator.

5. The apparatus of claim 4, wherein said guiding means comprises an at least substantially upright chute.

6. The apparatus of claim 1, wherein said feeding means defines an at least substantially horizontal path for the commodities and said platform has an upper side which is disposed at or close to the level of said path.

7. The apparatus of claim 6, further comprising means defining a barrier partially surrounding said platform and arranged to locate successive oncoming commodities in predetermined positions with reference to the platform.

8. The apparatus of claim 1 for accumulating stacks of commodites each of which has a predetermined height, wherein said means for moving said elevator up and down comprises means for lowering the elevator in stepwise fashion through distances each of which at least approximates said predetermined height.

9. The apparatus of claim 8 for accumulating stacks of commodities each of which constitutes a pile of superimposed sheets, wherein said lowering means is arranged to lower the elevator by more than two steps.

10. A method of accumulating stacks of sheet-like commodities in containers of the type having open tops, comprising the steps of advancing a series of discrete commodities along a predetermined path; arresting successive foremost commodities in a predetermined position at the general level of said path; individually effecting a stepwise gravitational decent of each of a preselected number of successive arrested commodities from the level of said path to a second level below the level of said path; lowering the commodities below said second level so that the first commodity of the preselected number descends alone and each following commodity descends with the proceding commodity of commodities whereby the thus descending commodities accumulate into a stack of superimposed commodities; placing a container below the stack; and effecting a gravitational descent of the grown stack into the container therebelow.

11. The method of claim 10, further comprising the step of imparting to each commodity a predetermined orientation in the course of the respective arresting step.

12. The method of claim 10, further comprising the step of laterally confining the commodities in the course of said stack accumulating step.

13. The method of claim 10, further comprising the step of laterally confining the stack during descent of the stack into the container.

* * * * *